United States Patent [19]

Anapliotis et al.

[11] Patent Number: 5,368,014
[45] Date of Patent: Nov. 29, 1994

[54] MODULAR ENDOSCOPE HAVING EASILY REPLACEABLE PARTS

[75] Inventors: Emmanuel Anapliotis, Berlin; Gisbert Schich, Ansbach, both of Germany

[73] Assignee: Effner Biomet GmbH, Berlin, Germany

[21] Appl. No.: 925,069

[22] Filed: Aug. 6, 1992

Related U.S. Application Data

[63] Continuation-in-part of Ser. No. 602,298, Nov. 21, 1990, Pat. No. 5,184,602.

[30] Foreign Application Priority Data

Aug. 8, 1991 [DE] Germany .................. 9109924[U]

[51] Int. Cl.⁵ ................................. A61B 1/00
[52] U.S. Cl. ............................ 128/4; 354/62
[58] Field of Search ............... 128/4, 6, 7, 8; 358/98; 354/62

[56] References Cited

U.S. PATENT DOCUMENTS

| | | |
|---|---|---|
| 4,624,243 | 11/1986 | Lowery et al. . |
| 4,655,569 | 4/1987 | Sims ........................ 354/62 |
| 4,736,733 | 4/1988 | Adair . |
| 4,838,247 | 6/1989 | Forkner . |
| 5,024,212 | 6/1991 | Bonnet et al. . |
| 5,152,278 | 10/1992 | Clayman ..................... 128/4 |
| 5,156,141 | 10/1992 | Krebs et al. ................. 128/4 |
| 5,168,863 | 12/1992 | Kurtzer ....................... 128/4 |
| 5,184,602 | 2/1993 | Anapliotis et al. ........... 128/6 |
| 5,188,094 | 2/1993 | Adair ....................... 128/4 X |

FOREIGN PATENT DOCUMENTS

| | | |
|---|---|---|
| 1696900 | 4/1955 | Germany . |
| 2062951 | 9/1971 | Germany . |
| 2328554 | 3/1976 | Germany . |
| 2637133 | 2/1978 | Germany . |
| 2825376 | 12/1978 | Germany . |
| 3014116 | 10/1980 | Germany . |
| 8019119 | 2/1981 | Germany . |
| 3429945 | 4/1985 | Germany . |
| 3341876 | 5/1985 | Germany . |
| 3504252 | 10/1988 | Germany . |
| 8814573 | 2/1990 | Germany . |
| 3918719 | 12/1990 | Germany . |
| 1400967 | 7/1975 | United Kingdom . |

Primary Examiner—Richard J. Apley
Assistant Examiner—Beverly A. Meindl
Attorney, Agent, or Firm—Spencer, Frank & Schneider

[57] ABSTRACT

An endoscope, particularly an arthroscope, preferably composed of an illumination module (17) and a viewing module (1) which can be connected together, with the viewing module (1) being provided with an optical system carrying shaft (2) which can be inserted into an interior cannula (18) in the viewing module (17), with the optical system carrying shaft (2) being part of a rotary optical system (3) that is surrounded by an optical system guide sleeve (5). The rotary optical system (3) is mounted in a manner secure against rotation and displacement within the optical system guide sleeve (5) and the viewing module includes a coupling device (9) which is connected with the optical system guide sleeve for connection with a removable optical funnel (12) on the side of the eyepiece.

14 Claims, 4 Drawing Sheets

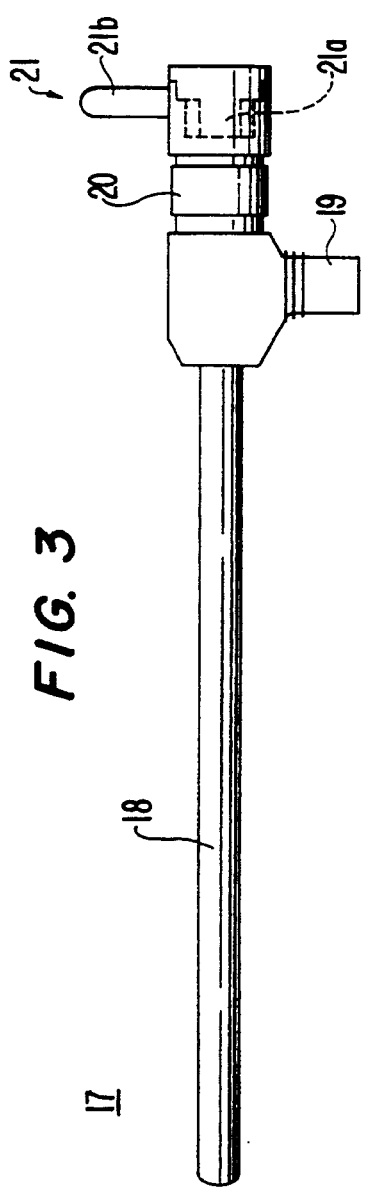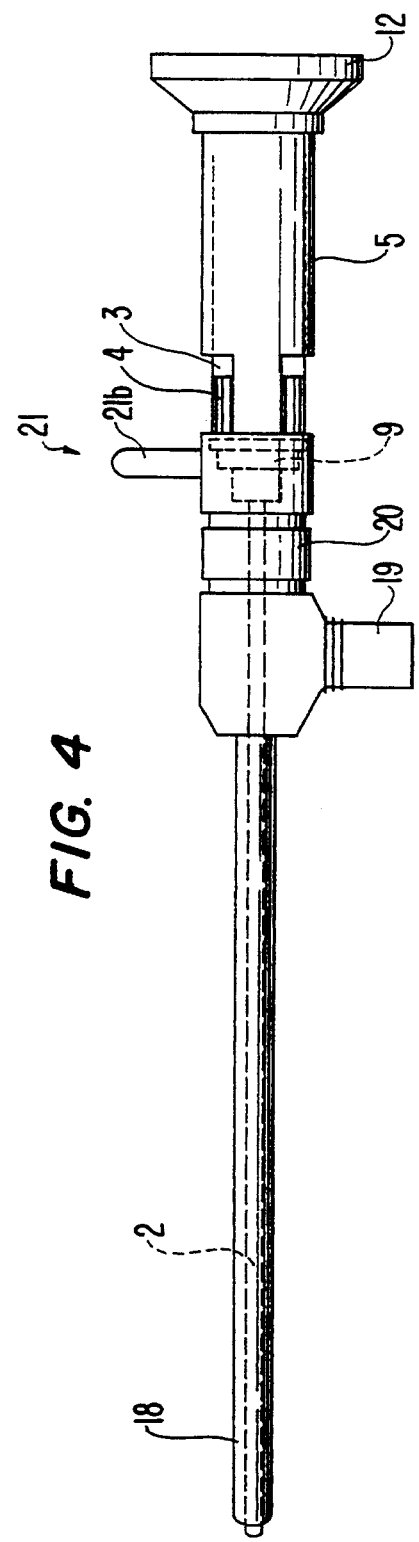

MODULAR ENDOSCOPE HAVING EASILY REPLACEABLE PARTS

CROSS REFERENCE TO RELATED APPLICATIONS

This application is a continuation-in-part of application Ser. No. 07/602,298, filed Nov. 21, 1990, having a PCT filing date of Nov. 19, 1989, and issued as U.S. Pat. No. 5,184,602 on Feb. 9, 1993.

BACKGROUND OF THE INVENTION

The invention relates to an endoscope composed of an illumination module and a viewing module which are adapted to be connected with one another, the viewing module being provided with an optical system carrying shaft insertable into an interior cannula of the illumination module.

Such endoscopes are employed to examine body cavities and, in the form of arthroscopes, serve to examine and treat joints, usually the knee joints, in that, upon introduction of the arthroscope, the interior of the joint can be viewed. Preferably for the diagnosis of meniscus injuries arthroscopy is a frequently employed procedure.

Since the interior of the joint is not only viewed but also illuminated, endoscopes, such as, for example, the endoscope disclosed in German Utility Model Patent DE-GM 88/14,573, are provided with preferably separate illumination and viewing modules which can be plugged together. The viewing module includes a shaft carrying the optical system, an objective lens to be introduced into the interior of the joint at the distal end of the shaft and an eyepiece at the proximal viewing end of the shaft, and can be pushed into the light shaft of the illumination module.

However, the drawback of the prior art endoscopes is that the viewing component must always be replaced completely if an optical system having a different viewing angle is required for the further examination or must be replaced in the case of a defect. In particular, if the optical system is changed, manipulations are always required in the sterile region as well as in the non-sterile region so that a cover separating the respective regions must also always be replaced.

SUMMARY OF THE INVENTION

It is the object of the invention to overcome the above-described drawbacks in an endoscope of the above-mentioned type in order to obtain an endoscope which, on the one hand, can be manufactured economically and in which, on the other hand, components can be exchanged without much effort—even under surgical conditions—with, in particular, the sterility in the surgical area remaining in effect.

This is accomplished by the present invention, according to which the viewing module comprises:

(a) a rotary optical system including the optical system carrying shaft;

(b) an optical system guide sleeve surrounding the rotary optical system such that the rotary optical system is rotatably and displaceably mounted within the optical system guide sleeve; and (c) an optical funnel removably attachable to the optical system guide sleeve; and (d) a guide sleeve coupling device provided on the optical system guide sleeve for removably attaching the optical funnel thereto.

The invention includes the realization that an advantageous endoscope can be created if the viewing module can be taken apart in such a way that the parts possibly requiring replacement are easily accessible and are exchangeable in such a way that, in the case of a defect, only the actually damaged components need to be replaced.

In particular, in such an exchange of the optical system, only a few components of the viewing module need to be removed and manipulated if the interior optical system which is connected with the shaft carrying the optical system is to be exchanged, with the connection with a viewing and illumination module remaining in effect in principle. Due to the fact that the inner portion of the optical system is configured as a rotary optical system, a rotation of this component relative to the stationary sleeve makes it possible to additionally select the direction of viewing if the viewing direction of the optical system is inclined relative to its axis. The complete viewing module composed of rotary optical system and optical system guide sleeve may have such exterior dimensions that it is exchangeable for one-piece viewing modules made by other manufacturers, making the endoscope compatible in this respect.

By making available a number of rotary optical systems having different viewing angles (angular range and "side viewing angle" with respect to the longitudinal axis) a greater field of application exists for the endoscope according to the invention. It is an additional advantage here if a video unit connected with the viewing module, particularly a camera, need not be moved and re-attached with every exchange process. In this connection, it is of primary significance that the camera is always disposed underneath a sterile covering sheet, with the point of connection between the recording unit and the viewing module lying within the sterile region of the covering sheet so that it is necessary to again sterilize the uncovered regions and the covering sheet after re-establishment of the connection.

Thus, in an endoscope system permitting different viewing angles, it is only necessary to hold available different rotary optical systems—whose exterior dimensions are uniform, however,—which can each be inserted individually into the optical system guide sleeve of the viewing module that is connected with the illumination module. The acquisition costs for such an endoscope having different optical systems are reduced considerably thereby and the effective period of use of an instrument can be increased considerably due to the relatively short time required for exchange and repair.

If the optical system is exchanged, a location of separation exists in the sterile region which is accessible for likewise sterile surgery personnel. A connected video camera remains on the non-sterile side underneath a covering so that the exchange of the optical system no longer requires re-sterilization or replacement of the covering of the camera which would be connected in each case with complicated and time consuming manipulations since non-sterile persons would have to access the sterile region with the additional danger of sterile persons being contaminated which would then have to subject themselves to a complicated scrubbing procedure.

The viewing module according to the invention comprises a rotary optical system including a shaft connected thereto for carrying the optical system. The optical system is disposed within an optical system guide sleeve. At its proximal end, that is, on the side of the eyepiece, the optical system guide sleeve is connected by means of a guide sleeve coupling device with an unscrewable optical funnel. At its distal end, the guide sleeve coupling device is provided with connecting elements by means of which the illumination module and the viewing module can be connected together. The viewing module is composed of the rotary optical system, the optical system guide sleeve, and the optical funnel. Due to the fact that only the optical system guide sleeve is fixed part of the viewing module, the rotary optical system connected with the optical system carrying shaft is easily accessible and exchanged through the opening created when the optical funnel is unscrewed.

If a video unit is connected directly or by way of an adapter with the optical funnel, the optical funnel is given such a configuration that its connections with the optical system guide sleeve as well as with the recording unit are releasable so that, after the optical funnel has been unscrewed, not only is the sterile viewing module separated from the non-sterile camera, the interior of the viewing module is also accessible for an exchange of optical systems.

The connection between the optical funnel and the optical system guide sleeve is preferably configured as a screw connection, while the connection between the optical funnel and the recording unit is preferably configured as a clamp or plug-in connection so as to facilitate the separation of the optical funnel on both sides. In this case, the clamp or plug-in connection between the recording unit and the optical funnel is released first in that the recording unit is removed from the endoscope. To accomplish this, only the position of the video unit is changed and not that of the endoscope. This is an important requirement for an endoscope that is inserted in the body since uncontrolled further penetration of the endoscope into the body cavity must be avoided due to the danger of injury to the patient. Then the now easily accessible optical funnel can be unscrewed from the optical system guide sleeve and the rotary optical system disposed within the sleeve and the optical system carrying shaft connected with it can be removed from the sleeve.

Due to it being possible to separate the optical funnel and the recording unit which is provided with a sterile covering at the corresponding adapter unit, it is possible in a favorable manner not to have to remove the sterile covering even if the optical funnel is quickly coupled to or decoupled from the recording unit and it is also not damaged.

BRIEF DESCRIPTION OF THE DRAWINGS

Other advantageous features of the invention are defined in the dependent claims and will be described in greater detail below together with a description of the preferred embodiment of the invention and with reference to the drawing figures, in which:

FIG. 3 is a side elevational view of an advantageous embodiment of the illumination module as part of the endoscope according to the invention;

FIG. 4 is a partially sectional, side elevational view of the endoscope according to the invention in the mounted state.

DETAILED DESCRIPTION OF THE INVENTION

Figure 1:
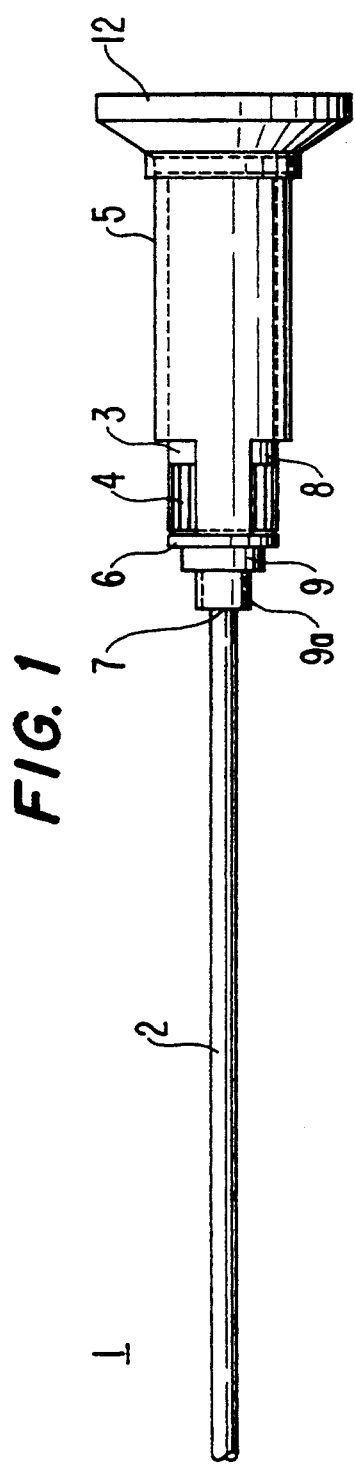
FIG. 1 is a side elevational view of an advantageous embodiment of the assembled viewing module as part of the endoscope according to the invention.
Figure 2:
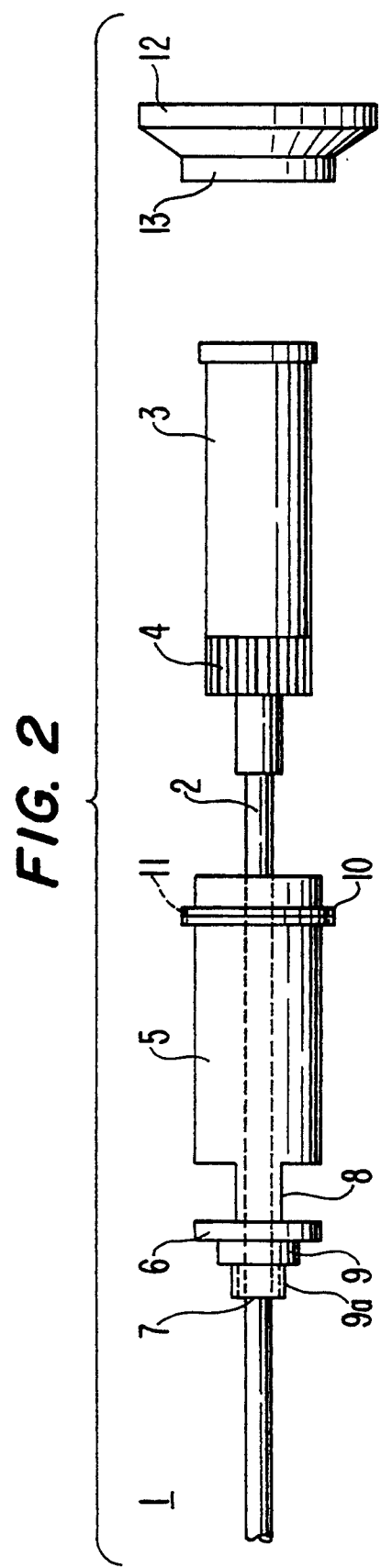
FIG. 2 is a further illustration of the viewing module of FIG. 1, with the rotary optical system being partially pulled out of the optical system guide sleeve.

The description below simultaneously makes reference to FIGS. 1 and 2, with FIG. 1 depicting the viewing module 1 in its assembled operational position and FIG. 2 the viewing module 1 separated in its individual components.

Viewing module 1 is composed of a rotary optical system 3 equipped with an optical system carrying shaft 2, an optical system guide sleeve 5 and an optical funnel 12 on the side of the eyepiece. In the region of optical system carrying shaft 2, rotary optical system 3 is given a rod shape and contains the lenses required for generating and transmitting an image. It constitutes a closed unit and is shown in FIG. 2 as partially withdrawn from optical system guide sleeve 5. Rotary optical system 3 is provided with a rotation ring 4 that is given a knurled edge for manual operation by means of which the optical system can be rotated within sleeve 5 (see FIG. 1), if the latter is held in its installed position by the further components of the endoscope as described below. For this purpose, the wall of the optical system guide sleeve 5 is provided with at least one corresponding recess 8 through which the knurled rotation ring 4 of rotary optical system 3 is accessible from the outside and can be turned manually. By rotating the optical system about its longitudinal axis, the direction of viewing of the objective lens can be changed if the latter has a direction of view at its object side which deviates from the longitudinal axis. In addition, the angle of view can also be changed by selecting an optical system that has the appropriate viewing angle. The same applies for the angular range to be viewable.

At its distal end 6, the optical system guide sleeve 5 is provided with an aperture 7 through which the optical system carrying shaft 2 of rotary optical system 3 is inserted when viewing module 1 is assembled. In addition, optical system guide sleeve 5 is provided with an illumination module coupling device 9 with which it is connected with an illumination module 17 that will be described in greater detail in connection with FIG. 3.

The coupling device 9 of the optical system guide sleeve is preferably configured as a threaded attachment 9a equipped with an external thread which can be screwed into a corresponding bore 21a provided with an internal thread in the illumination module 17 according to FIG. 3. However, coupling device 9, 21a may also be configured differently, for example, as a plug-in or bayonet connection. Optical system guide sleeve 5 and the illumination unit can thus remain connected with one another for an exchange of the rotary optical system so that the latter, on the one hand, is rotatably mounted but, on the other hand, can be easily exchanged without the illumination unit having to be removed. If required, the rotary optical system can be arrested by means of an arresting device 21 which, particularly in the form of a radially displaceable pin whose interior end engages in a corresponding non-illustrated recess or in some other way, forms a rotation lock so that the viewing direction remains unchanged.

Figure 5:
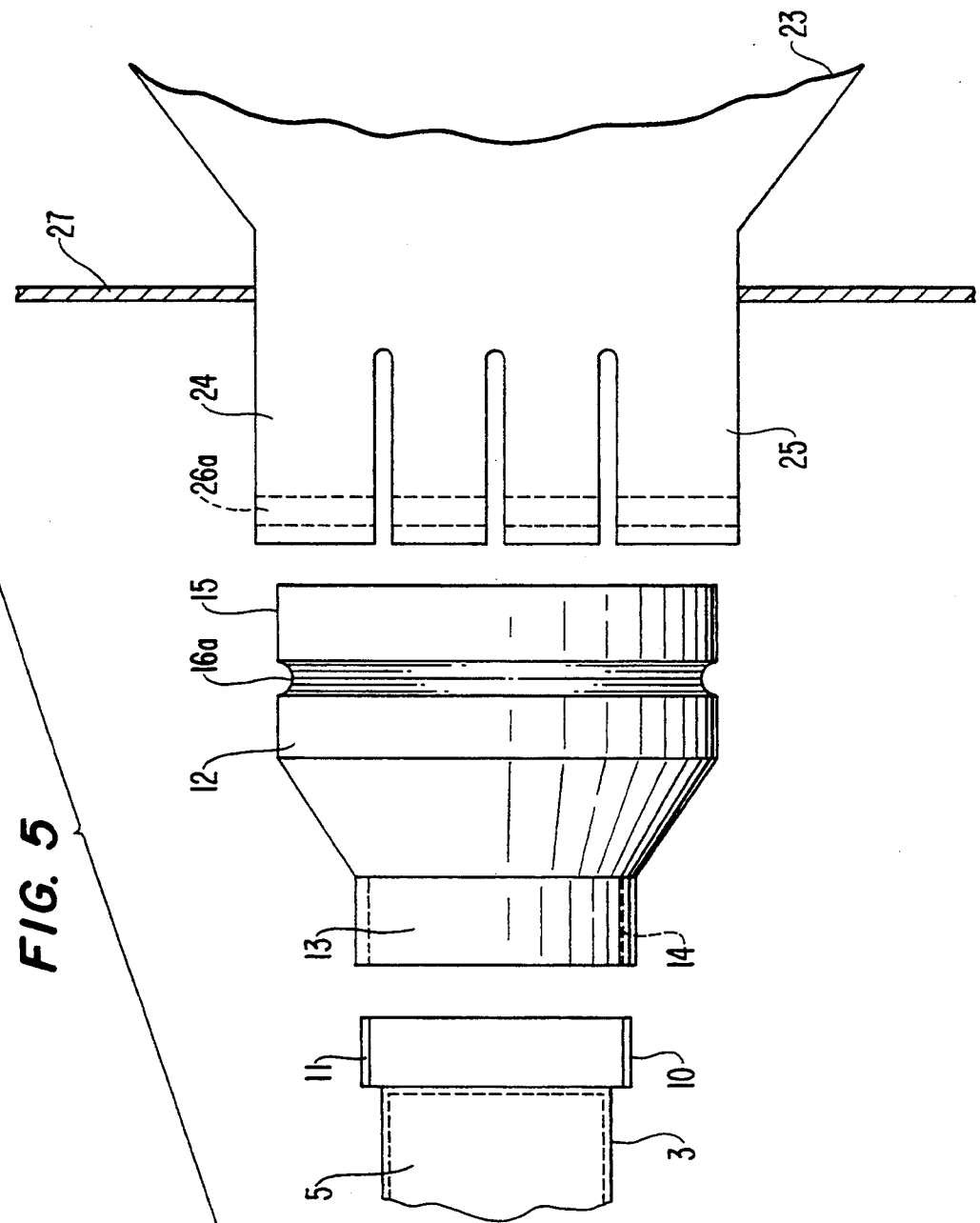
FIG. 5 is an enlarged, side elevational view of an optical funnel as the viewing module element which is disposed on the side of the eyepiece and is connected with a display unit and with the viewing module by means of a bead on the display unit mating with a groove on the optical funnel.

On the side of the eyepiece, an optical funnel 12 is connected with optical system guide sleeve 5, with the function of the optical funnel 12 being described in greater detail below in connection with FIG. 5. For the assembly of viewing module 1, optical system guide sleeve 5 is introduced from the eyepiece end 6 of optical system guide sleeve 5 into the optical system carrying shaft 2 until the rotary optical system 3 abuts. Then the eyepiece side of optical funnel 12 is screwed to the end of optical system guide sleeve 5. Thus, optical system guide sleeve 5 forms an encasement for the rotary optical system, with its opening on the side of the eyepiece being closed by the optical funnel.

Thus optical system guide sleeve 5 forms an encasement for the manually operatable rotation ring 4 of the rotary optical system that is stationary relative to the optical system and is equipped with at least one opening 8 providing access to the rotation ring. The stationary optical system guide sleeve thus is provided with a protecting sleeve connection means for a protective sleeve or tube (here: illumination unit 17) which surrounds the optical system carrying shaft 2 of the rotary optical system, on the one hand, and a camera connection (here: optical funnel 12) so that the rotary optical system can be rotated with manual access in the thus formed "chamber" while the outer components including the camera connection are stationary.

The illumination module 17 shown in FIG. 3 into which the viewing module can be inserted is composed of a cannula 18 that can be inserted into the interior of the joint and an attached illumination member 19 which serves to connect self-supporting or flexible light conducting cables for the purpose of supplying light; a module 20 of a suction and rinsing device for the supply and discharge of rinsing substance or extracted fluids; and a second coupling device 21 for coupling illumination module 17 to the first coupling device 9 attached to the optical system guide sleeve 5 of viewing module 1. The coupling device 9 includes—as mentioned—additional means for locking the rotary optical system 3 which is rotatably mounted in optical system guide sleeve 5.

The embodiment of the endoscope according to the invention shown in FIG. 4 can be installed with only a few manipulations by introducing the optical system carrying shaft 2 into cannula 18 and by coupling illumination module 17 to viewing module 1. If rotary optical system 3 is removed because it is damaged or because another rotary optical system 3 having a different viewing angle is required, it is merely necessary to unscrew the optical funnel 12 from the optical system guide sleeve 5 in order to be able to remove the rotary optical system 3, which has already been unlocked by means of coupling device 21, from the endoscope. The new rotary optical system 3 is reinserted in the reverse sequence.

The configuration of the optical funnel 12 according to the invention and its connection with recording unit 23 and optical system guide sleeve 5 will be described with reference to FIG. 5.

Figure 6:
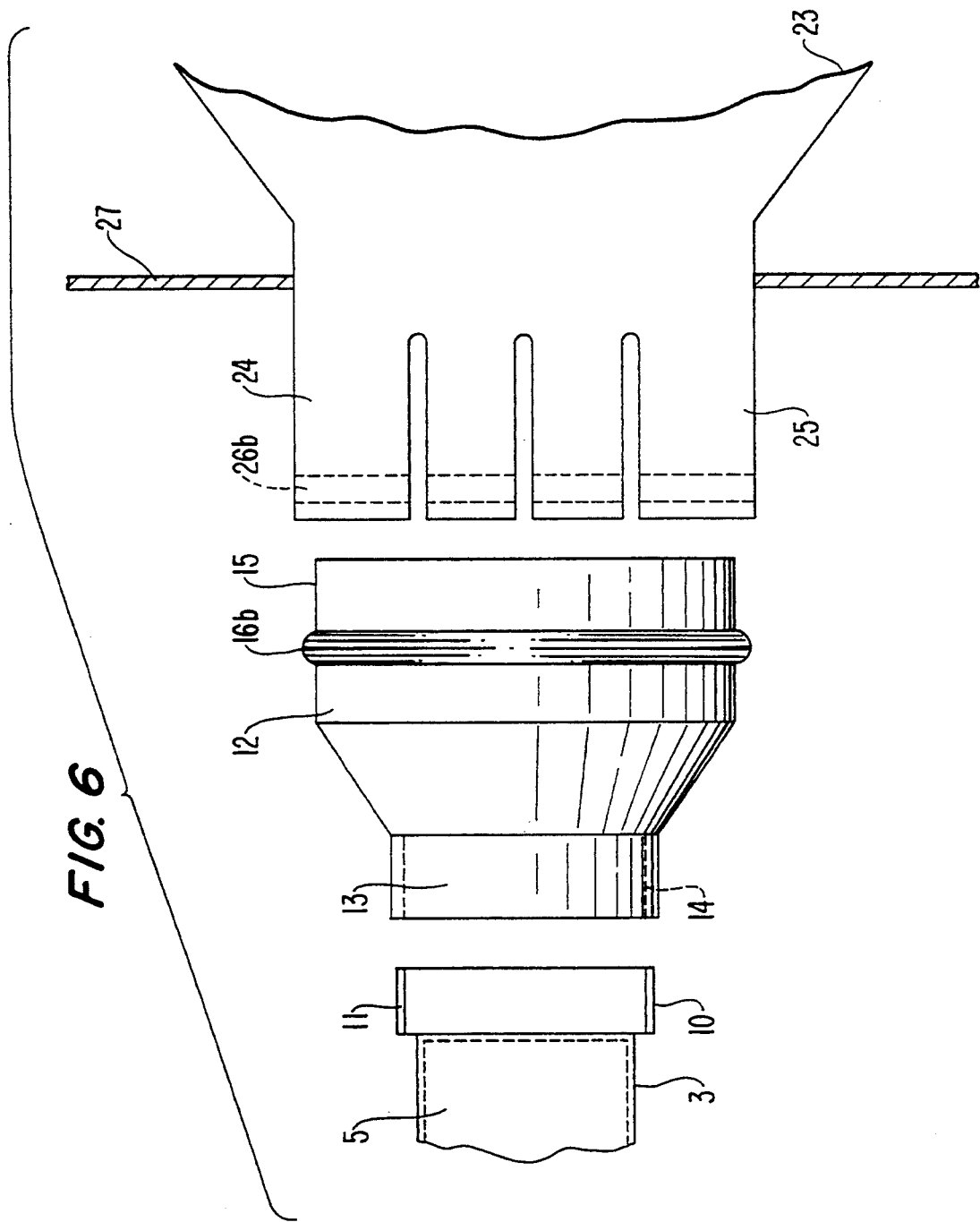
FIG. 6 is a view similar to FIG. 5, with the connection between the display unit and the viewing module being effected by means of a bead on the optical funnel and a groove on the display unit.

Optical funnel 12, which serves as an eye cup or camera connection and protects rotary optical system 3 against damage is provided at its distal end with an optical funnel threaded connection 13 that is equipped with an internal thread 14 and which can be screwed onto optical system guide sleeve 5 which is equipped with a guide sleeve threaded connection 10 having a corresponding external thread 11. Optical funnel 12 may also be connectable in a different manner, for example by way of a plug-in or bayonet connection, with optical system guide sleeve 5. Since the optical funnel 12 of the endoscope is additionally configured to be connectable with a recording unit 23, the radially exterior surface 15 of the funnel is provided with a video unit attachment means such as an annular groove 16a. The connecting member, or adapter member 24, which is fixed to recording unit 23 and at which is fastened a covering 27 that separates the sterile region (on the side of the objective lens) from the non-sterile region (including the video camera), is given a corresponding annular bead 26a on its interior face 25. In a preferred modification the adapter member is slotted in the longitudinal direction so that insertion of the optical funnel 12 into adapter member 24 is facilitated. As an alternative, optical funnel 12 may also be provided with an annular bead 16b on its exterior surface 15 and adapter member 24 with a corresponding annular groove 26b. This variation is FIG. 6 illustrated in the drawing figures.

It can be seen that, for an exchange of the rotary optical system, covering 27 can stay connected with adaptor, or camera attachment 24 so that no manipulations, that is, no manipulations in the non-sterile region, are required since the opening for insertion of rotary optical system 3 into optical system guide sleeve 5 receiving it lies exclusively on the sterile side. Thus it is also not necessary to make available a covering 27 for every exchange of objective lenses.

In the endoscope according to the invention the optical system guide sleeve 5 thus constitutes an essentially closed chamber in which a rotation ring 4 is arranged to be accessible from the outside as a manual actuation means for rotation of the rotary optical system 3, with the optical system guide sleeve, which is stationary with respect to the rotary optical system, being provided at its one end with adaptor means for the likewise stationary connecting member 24 constituting a video adapter and at its other end with a sleeve for protection of the optical system carrying shaft 2 of the rotary optical system 3, or with connecting means for such a sleeve.

The invention is not limited in its embodiments to the above-described preferred embodiment. Rather, a number of variations are conceivable which take advantage of the described solution even for basically different configurations.

We claim:

1. In an endoscope composed of an illumination module and a viewing module which are adapted to be connected with one another, the viewing module including an optical system carrying shaft insertable into an interior cannula of the illumination module, the improvement wherein said viewing module further comprises:

(a) a rotary optical system including said optical system carrying shaft;

(b) an optical system guide sleeve surrounding said rotary optical system such that said rotary optical system is rotatably and displaceably mounted within said optical system guide sleeve;

(c) an optical funnel removably attachable to said optical system guide sleeve; and (d) a guide sleeve coupling device provided on said optical system guide sleeve for removably attaching said optical funnel thereto.

2. An endoscope according to claim 1, wherein said guide sleeve coupling device includes threads to form a screw connection with said optical funnel.

3. An endoscope according to claim 1, wherein said guide sleeve coupling device includes external threads disposed on said optical system guide sleeve; and said optical funnel includes internal threads for coupling with the external threads of said guide sleeve coupling device to form a screw connection.

4. An endoscope according to claim 3 and further including an adapter member for a video unit to be used with said endoscope, said optical funnel including a video unit attachment means for attaching said optical funnel to said adapter member.

5. An endoscope according to claim 4, wherein said video unit attachment means includes means for forming a plug-in connection.

6. An endoscope according to claim 4, wherein said video unit attachment means includes means for forming a clamp connection.

7. An endoscope according to claim 4, wherein said video unit attachment means comprises an annular groove disposed on an exterior surface of said optical funnel; and said adapter member includes an annular bead disposed on an interior surface of said adapter member and adapted to be mated with said annular groove such that said optical funnel can be plugged into said adapter member.

8. An endoscope according to claim 4, wherein said video unit attachment means comprises an annular bead disposed on an exterior surface of said optical funnel; and said adapter member includes an annular groove disposed on an interior surface of said adapter member and adapted to be mated with said annular bead such that said optical funnel can be plugged into said adapter member.

9. An endoscope according to claim 4 and further including a sterile covering for surrounding a video unit to be used with said endoscope, said sterile covering being adapted to be fastened to said adapter member such that a connection between said optical funnel and said adapter member is disposed within a sterile region of said sterile covering.

10. An endoscope according to claim 1 and further including an essentially closed chamber formed by said optical system guide sleeve, wherein said optical system guide sleeve includes a distal end and said viewing module further comprises a rotation ring for allowing manually actuable rotation of said rotary optical system, said rotation ring being disposed in said essentially closed chamber and being accessible for manual actuation from an outside region of said chamber, said endoscope further including:

(a) a video unit attachment means for connecting said viewing module to an adapter member of a video unit to be used with said endoscope, said video unit attachment means being disposed at a proximal end of said optical system guide sleeve, said optical system guide sleeve being stationary with respect to said rotary optical system; and (b) a protecting sleeve for protecting said optical system carrying shaft of said rotary optical system, said protecting sleeve being disposed at said distal end of said optical system guide sleeve.

11. An endoscope according to claim 10, wherein said optical system guide sleeve includes a protecting sleeve connecting means at the distal end thereof, said protecting sleeve connecting means being for connecting said protecting sleeve to said optical system guide sleeve.

12. An endoscope according to claim 10, wherein said optical system guide sleeve includes at least one opening in in its wall for permitting access to said rotation ring for a manual actuation thereof, said rotation ring including a knurled ring and permitting an adjustment of a rotary position of said rotary optical system relative to said optical system guide sleeve.

13. An endoscope according to claim 1, wherein said optical system guide sleeve includes a removal opening therein through which said rotary optical system can be removed from said optical system guide sleeve, said optical funnel sealing said removal opening.

14. An endoscope according to claim 1, wherein said viewing module and said illumination module are arrestable relative to one another, said optical system guide sleeve comprising a threaded attachment and said illumination module comprising a corresponding threaded bore for connecting said optical system guide sleeve with said illumination module such that said optical system guide sleeve cannot rotate with respect thereto.

* * * * *